(12) United States Patent
Ho et al.

(10) Patent No.: US 8,758,811 B2
(45) Date of Patent: Jun. 24, 2014

(54) BIOFUNCTIONALIZED PHOSPHOLIPID-CAPPED MESOPOROUS SILICA NANOSHUTTLES FOR TARGETED DRUG DELIVERY

(75) Inventors: Ja-An Ho, Hsinchu (TW); Li-Sheng Wang, Hsinchu (TW); Chia-Min Yang, Hsinchu (TW); Li-Chen Wu, Nantou (TW)

(73) Assignee: National Tsing Hua University, Hsinchu (TW)

( * ) Notice: Subject to any disclaimer, the term of this patent is extended or adjusted under 35 U.S.C. 154(b) by 232 days.

(21) Appl. No.: 12/952,094

(22) Filed: Nov. 22, 2010

(65) Prior Publication Data

US 2011/0123601 A1 May 26, 2011

(30) Foreign Application Priority Data

Nov. 23, 2009 (TW) .............................. 098139728 A

(51) Int. Cl.
| | | |
|---|---|---|
| *A61K 9/127* | (2006.01) | |
| *A61K 51/12* | (2006.01) | |
| *A61K 38/16* | (2006.01) | |
| *A61K 39/395* | (2006.01) | |
| *A61K 38/18* | (2006.01) | |
| *A61K 31/7088* | (2006.01) | |
| *A61K 31/519* | (2006.01) | |
| *A61P 43/00* | (2006.01) | |
| *A61P 37/00* | (2006.01) | |
| *A61K 47/06* | (2006.01) | |
| *B82Y 5/00* | (2011.01) | |

(52) U.S. Cl.
USPC ........ 424/450; 424/12.1; 424/9.6; 424/178.1; 514/1.1; 514/7.6; 514/44 R; 514/249; 514/785; 977/773; 977/783

(58) Field of Classification Search
None
See application file for complete search history.

(56) References Cited

U.S. PATENT DOCUMENTS

2006/0018966 A1* 1/2006 Lin et al. ...................... 424/484

OTHER PUBLICATIONS

Koole et al (Bioconjug. Chem. 2008; 19(12): 2471-2479).*
Xie et al. (J. Am. Chem. Soc. 2005; 127: 7480-7488).*
Lu et al. (SMALL 2007, 3(8):1341-1346).*
Pinto-Alphandary et al (International Journal of Antimicrobial Agents. 2000; 13: 155-168).*
Schooneveld et al. (Nano Letters 2008; 8(8): 2617-2525).*
Slowing et al (Advanced Drug Delivery Reviews. 2008: 60(11): 1278-1288).*
Juewen Liu et al., Porous Nanoparticle Supported Lipid Bilayers (Protocells) as Delivery Vehicles, J. Am. Chem. Soc. 2009, vol. 131, No. 4, 1354-1355, published on Web Jan. 12, 2009.
Notice of Allowance of Taiwan counterpart application (TW 09813972) dated Nov. 30, 2012, which has been granted patent (TW I 383808, issued on Feb. 1, 2013 ).

* cited by examiner

*Primary Examiner* — Scott Long
(74) *Attorney, Agent, or Firm* — WPAT, P.C.; Anthony King; Kay Yang

(57) ABSTRACT

The present invention provides a multilayer vehicle, including a mesoporous silica core and a lipid bilayer coating thereon. Hydrophobic molecules are formed between the silica core and lipid layer. Additionally, methods and uses of the multilayer vehicle are also provided.

8 Claims, 16 Drawing Sheets

BIOFUNCTIONALIZED PHOSPHOLIPID-CAPPED MESOPOROUS SILICA NANOSHUTTLES FOR TARGETED DRUG DELIVERY

FIELD OF THE INVENTION

The present invention relates to a multilayer vehicle including a mesoporous silica core and a lipid layer encapsulated thereon, and a relative preparation method and the uses.

BACKGROUND OF THE INVENTION

Although there are a plenty of researches in respect of mesoporous silica nanoparticles (MSNs), in particular to the researches of drug carrier or controlling release, there are few researches to discuss aggregation phenomenon or non-specific adsorption, and the applications on targeted delivery are almost absent. At present, the method for solving aggregation phenomenon in the literatures is to modify phosphate group with negative charge on the surface of MSNs, and aggregation could be slightly solved by this method. Recently, it is published that the bilayer is adsorbed on the surface of MSNs by fusion. Although the aggregation and non-specific adsorption phenomena of MSNs are not discussed in the literatures, the principle is similar to the present invention. Therefore, it is supposed the present invention could have the similar results.

Previous study presents that MSNs successfully targeting to the target cells. Jessica et al. published that the dendrimers are modified on the surface of MSNs, folic acid conjugates the terminal of the dendrimers, and thus this prepared MSNs has function on targeting to HeLa cells.

The issue of the prior art lies in that the modification on small molecules does not benefit to prevent the non-specific adsorption although it can solve the aggregation by increasing the surface charges of MSNs, but the non-specific adsorption come off worse. Therefore, if the problem remain unsolved, and the MSNs can not be applied in targeted drug delivery.

Although fusion is convenient, it limits in many conditions, such as the fusion of liposome having the charge opposite to the charge of MSNs, and then derivation on this composition and the re-modification would be relatively impossible. Furthermore, the professional synthetic technology is necessary to dendrimers, and the preparation of dendrimers is not simple and yet, whether the macromolecule modified MSNs can successfully release the loaded drug should be evaluated.

SUMMARY OF THE INVENTION

MSNs cannot be applied in target drug carrier due to the aggregation in the physiological environment and the non-specific adsorption to the biomolecule (e.g. protein). Therefore, the solution to these two problems might be possible to make MSNs toward in vivo drug research and development.

The advantages of liposome and MSNs are combined in the present invention to improve MSNs aggregation and mitigate non-specific adsorption of protein on MSNs. The fluorescent value decreases to 27.5% after cotreatment of the regular MSNs and IgG-FITC (immunoglobulin G-fluorescein isothiocyanate), indicating 72.5% protein non-specifically adsorbed on the surface of bare/unmodified MSNs. However, the remaining fluorescent strength is about 74% if protein is mixed with phospholipid-coated MSNs, which effectively decrease the non-specifically adsorbed protein to 26%. Furthermore, the outermost layer of phospholipids conjugates the functional molecules, such as folic acid, on demand to achieve the advantage of multi-functions.

MSNs has rigid structure, but aggregation is easily happened with each other. Although liposome owns high bio-compatibility and water solubility, the elastic structure results in the leakage of the encapsulated material due to the changes of surrounding environment. In the present invention, a lipid bilayer (similar to liposome structure) on the surface of MSNs is formed after a hydrophobic modification of silane onto the bare MSN surface. The problem of MSNs aggregation can be efficiently improved and the non-specifically adsorbed protein on MSNs surface can be decreased at the same time.

Since the composite material of the present invention has "ordered" porous structure, which forms the lipid bilayer on MSNs surface and decreases the phenomena, aggregation and non-specific adsorption, etc., the composite material could be developed as the targeted drug carrier/shuttle.

The most difference between the present invention and the prior art lies in that the highly-biocompatible phospholipid-coated MSNs enable the increase in the water solubility and the bio-compatibility. Furthermore, in the present invention, the outermost phospholipids can be replaced on demand, such as different modification of the target molecules, contrast agents, etc., to achieve the advantage of multi-functions.

The term, "mesoporous silica nanoparticle (MSN)", of the present invention is referred to spherical nanoparticle having porous structure, which has a pore size ranged between 2 nm and 50 nm.

The term, "liposome", of the present invention is referred to spherical carrier coated lipid bilayer, and lipid bilayer is self-assembled from phospholipids in the water. Since phospholipids have similar structure to the components of cell membrane, this material has relatively high bio-compatibility.

Therefore, a multilayer vehicle is provided in the present invention, which includes a mesoporous silica core and a lipid layer, and the hydrophobic molecule is formed between the mesoporous silica core and the lipid layer (FIG. 1a). In the preferred embodiment of the present invention, the surface of liposome conjugates a functional molecule for recognizing the target cell, such as target molecule, genetic material, aptamer, protein, antibody, contrast agent and folic acid, etc.

In the preferred embodiment of the present invention, the mesoporous silica core is a spherical nanoparticle having a porous structure ranged between 2 nm and 50 nm. In a more preferred embodiment of the present invention, the porous structure is an "ordered" porous structure. In the best embodiment of the present invention, the pore of the mesoporous silica core loads the drug.

The method for preparing the above multilayer vehicle is also provided in the present invention, and the method includes steps of: (a) hydrophobically modifying a surface of a silica nanoparticle; and (b) self-assembled lipid layer coated on the silica nanoparticle via hydrophobic interaction.

In the preferred embodiment of the present invention, the hydrophobic modification is to conjugate a terminal of a hydrophobic layer (or a hydrophobic molecule) on the surface of the silica nanoparticle. In the more preferred embodiment of the present invention, the hydrophobic layer is 13-(chlorodimethylsilanemethyl)-heptacosane, polycaprolactone (PCL), polyvalerolactone (PVL), poly(lactide-co-glycolide) (PLGA), polylactic acid (PLA), polybutyrolactone (PBL), polyglycolide or polypropiolactone (PPL). In the best embodiment of the present invention, the hydrophobic molecule is 13-(chlorodimethylsilanemethyl)-heptacosane.

In the preferred embodiment of the present invention, the method further includes a step (c) of conjugating a functional molecule on the lipid layer. In the more preferred embodiment of the present invention, the functional molecule includes target molecule, genomic material, aptamer, protein, antibody, contrast agent and folic acid. In the best embodiment of the present invention, the functional molecule is folic acid.

In the preferred embodiment of the present invention, an active material is added into the pore of the nanoparticle of the above multilayer vehicle for being the carrier. In the more preferred embodiment of the present invention, the active material includes drug, fluorescent agent, protein, polypeptide, radioactive material, constrast agent, growth factor or genomic material. In the best embodiment of the present invention, the active material is drug.

The term, "comprises", "have", "include" or "consist of", used in the specification and claims is referred to closed or open form, and does not exclude the unquoted elements, steps or methods.

The term, "inhibit", "eliminate", "prevent" or the equivalence used in the specification and claims include any determined decrease or the complete inhibition to achieve the desired result.

The term, "effective", used in the specification and claims is referred to the necessary, the anticipated and the expected result to be achieved.

The above objectives and advantages of the present invention will become more readily apparent to those ordinarily skilled in the art after reviewing the following detailed descriptions and accompanying drawings, in which:

DETAILED DESCRIPTION OF THE PREFERRED EMBODIMENT

The present invention will now be described more specifically with reference to the following Embodiments. It is to be noted that the following descriptions of preferred Embodiments of this invention are presented herein for purpose of illustration and description only; it is not intended to be exhaustive or to be limited to the precise form disclosed.

Embodiment 1: Synthesis of Phospholipid-coated Mesoporous Silica Nanoparticle (LipoFMSN)

A. Synthesis of Mesoporous Silica Nanoparticle (MSN)
 1. The adequate amount of 3-aminopropyltriethoxysilane (APTES) is dissolved in ethanol, and the adequate amount of fluorescein isothiocyanate (FITC) is added therein to mix well to form a ethanol solution of FITC-silane.
 2. Cetyl trimethylammonium bromide (CTAB) is dissolved in deionized water, and sodium hydroxide (NaOH) is added therein to mix well.
 3. After the adequate amount of tetraethoxysilane (TEOS) is diluted with ethanol, the above-mentioned solution (from step 2) is dropped therein to mix well.
 4. The FITC-silane solution (from step 1) is dropped therein to mix continuously.
 5. TEOS is diluted with ethanol and the diluted TEOS is slowly dropped into the above-mentioned solution (from step 4) to stir for 1 hour.
 6. The above solution is aged for 1 day in the oven.
 7. The product is harvested using vacuum filtration, and the product is resolved in hydrochloride/ethanol and heated to reflux at 70° C.
 8. Step 7 is repeated.
 9. The product, fluorescent-conjugated MSN (FMSN), is harvested using vacuum filtration and is resolved in ethanol.

B. Surface Hydrophobization:
 1. The adequate amount of 13-(chlorodimethylsilanemethyl)-heptacosane is dissolved in chloroform ($CHCl_3$), and the adequate amount of FMSN is added therein to mix well.
 2. After the reaction is accomplished, $CHCl_3$ is removed using reduced pressure concentrator and is resolved with hexane. The supernatant is removed by centrifuging at 16,000 rpm, and the intermediate is washed with hexane.
 3. Step 2 is repeated thrice, and the product is harvested with drying and nominated as m-FMSN.

C. Phospholipid Encapsulation:
 1. The adequate amounts of dipalmitoylphosphatidylcholine (DPPC) and 1,2-bis(diphenylphosphino)ethane-polyethylene glycol 2000 (DPPE-PEG 2000) are dissolved in $CHCl_3$.
 2. Next, m-FMSN is dissolved in the organic solvent.
 3. The above two solutions are mixed after sonication, and the mixture is continuously mixed using sonication for 10 minutes.
 4. The organic solvent is removed using vacuum evaporation after the thin film is formed.
 5. The adequate buffer is added and is sonicated for 1 hour.
 6. The supernatant is removed at high speed centrifugation for 10 minutes, and the residue is washed with adequate buffer.
 7. The product is reserved in the adequate buffer after Step 6 is repeated thrice.

Figure 1A:
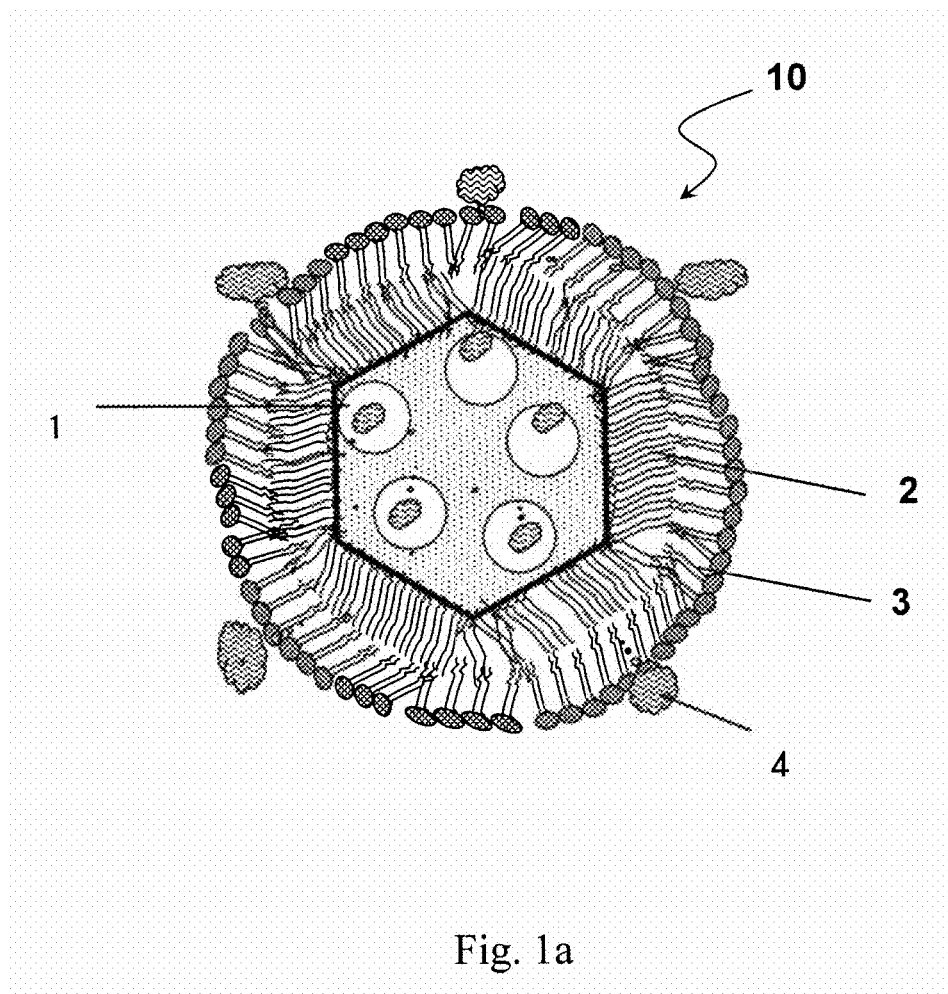
FIG. 1a illustrates the structure of the multilayer vehicle for the phospholipid-coated mesoporous silica nanoparticle.
Figure 1B:
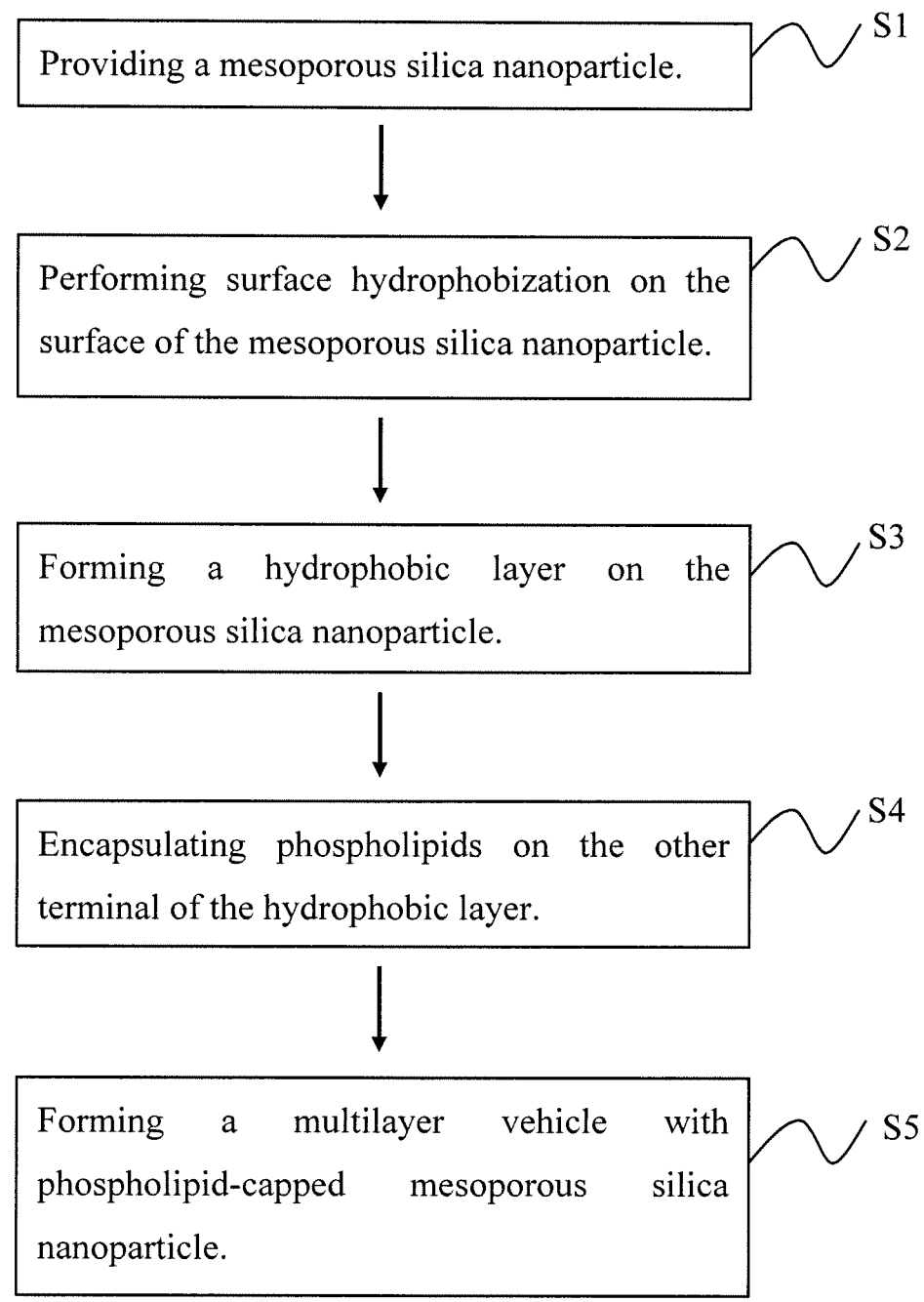
FIG. 1b illustrates the method for synthesizing the multilayer vehicle of the phospholipid-coated silica mesoporous nanoparticle.

As shown in FIG. 1b, about 200 nm of the fluorescence-conjugated MSN, abbreviated as FMSN, is synthesized in the present invention for observation. Next, self-assembled phospholipids coated on the FMSN by surface hydrophobization, and the FMSN owns the targeted capability by conjugating phospholipids where its end conjugates folic acid.

Embodiment 2: Identification of MSNs

Figure 2A:
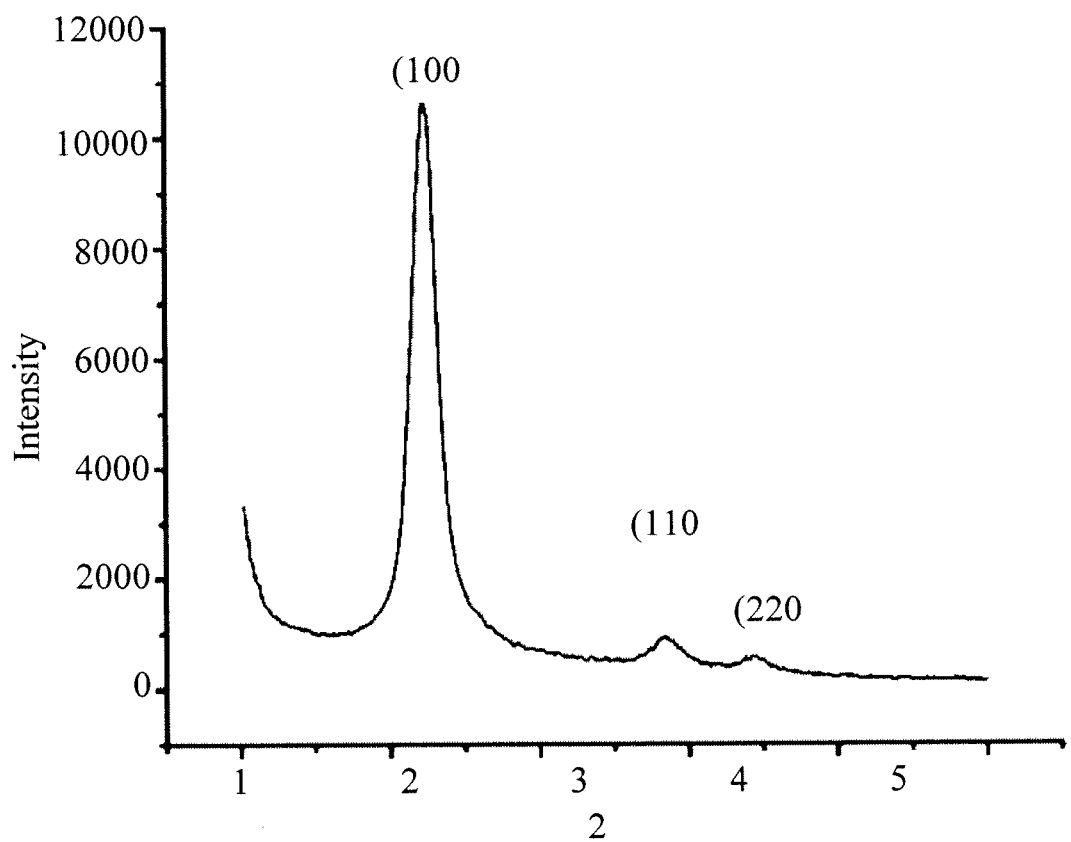
FIGS. 2a to 2c illustrate the identification of the mesoporous silica nanoparticle.
Figure 2B:
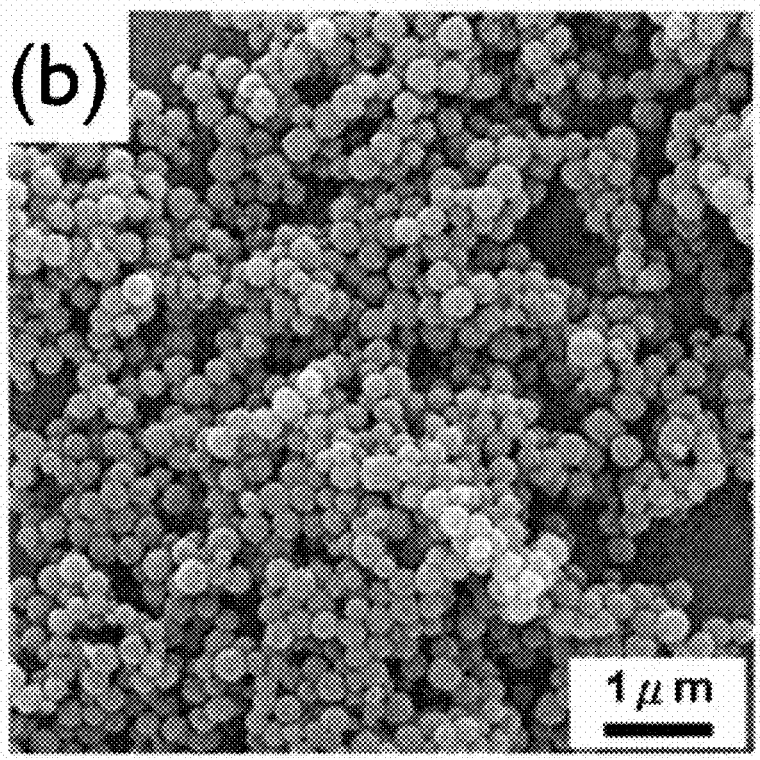
Figure 2C:
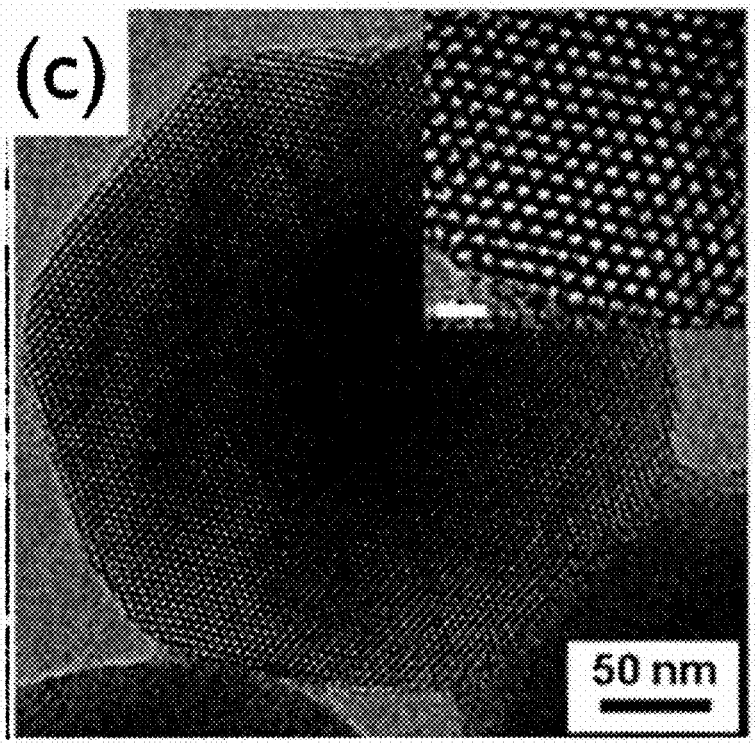

FIG. 2a illustrates the X-ray diffraction spectrum of FMSN. The small angle X-ray diffraction is used to determine the ordered arrangement of the mesopores in the material, and the diffraction peaks can be indexed as the 100, 110 and 220 reflections from a 2-dimensional hexagonal p6 mm mesostructure. FIG. 2b illustrates the scanning electron microscopy of FMSN, which is used to determine its shape and size as a spherical nanoparticle of 200 nm in diameter. FIG. 2c illustrates the transmission electron microscopy of FMSN, where the ordered mesostructure of FMSN can be clearly observed, and the pore size is about 3 nm.

Figure 3:
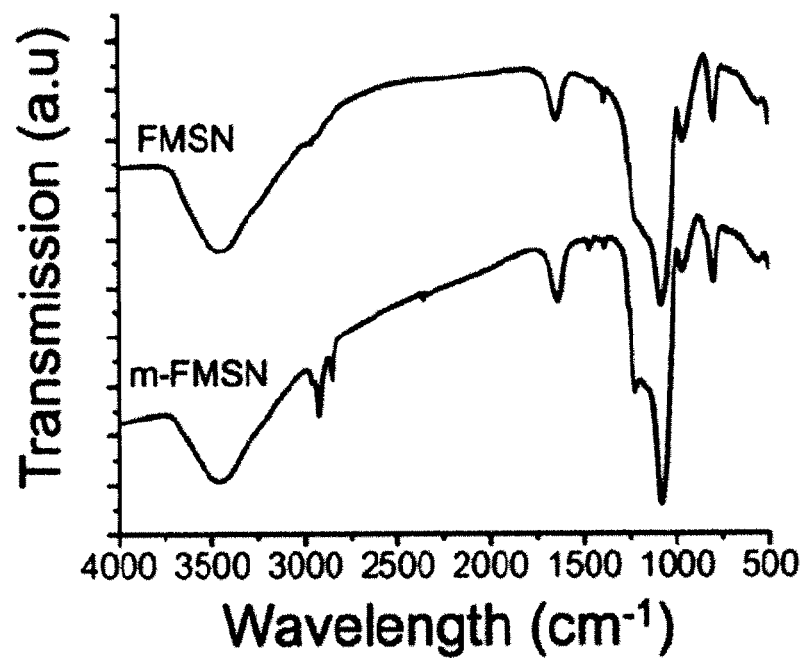
FIG. 3 illustrates the comparison between FMSNs before and after the surface hydrophobization.

FIG. 3 schematically illustrates the infrared absorption spectrum of FMSN. Whether the surface of FMSN has C—H stretching can be determined by observing the absorption peak at 2800~3000 cm$^{-1}$. Comparing the spectra before or after the hydrophobization, it can be identified that the hydrophobized FMSN (m-FMSN) carries more $CH_2$ groups and thus generates an absorption signal at 2800~3000 cm$^{-1}$ to prove the success of hydrophobization modification. The difference on water solubility before and after the hydrophobization lies in that the original hydrophilic bare-FMSN separates as two layers in the solution, and FMSN with the surface hydrophobization will disperse in the hydrophobic solvent (chloroform).

Figure 4:
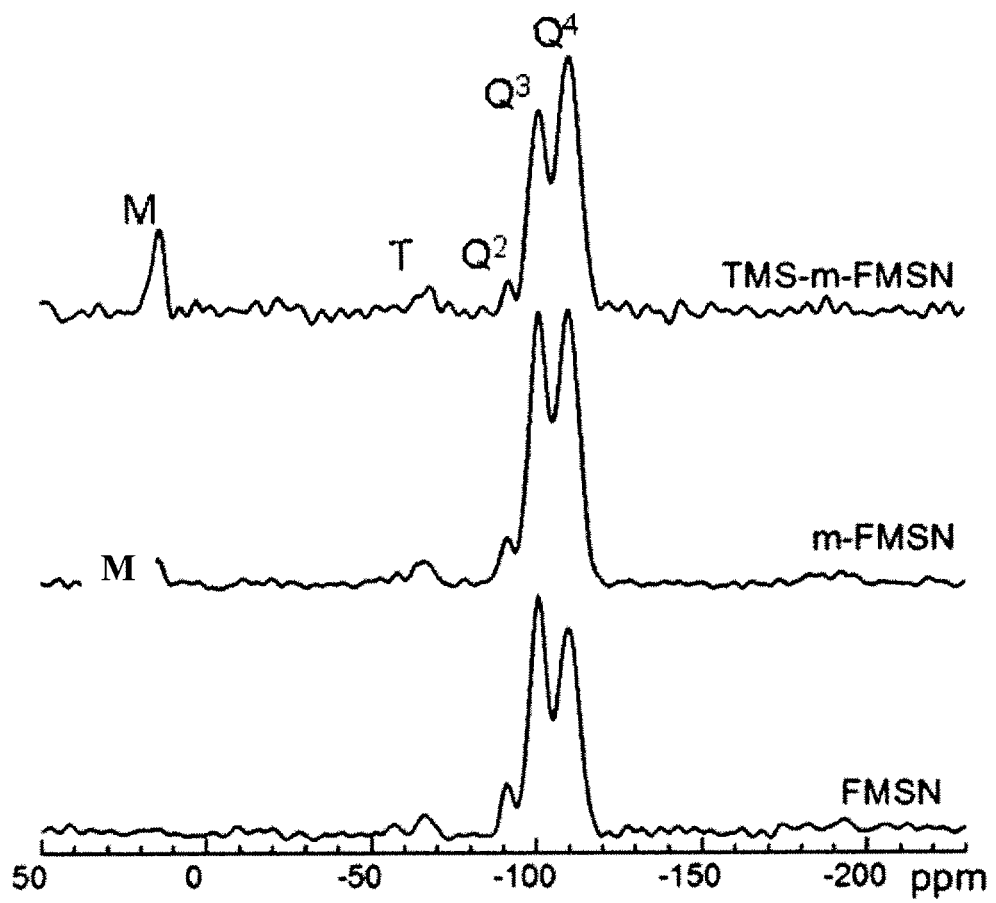
FIG. 4 illustrates the $^{23}$Si-solid state nuclear magnetic resonance spectrum of the FMSN before and after the phospholipid modification.

As shown in FIG. 4, since the surface of the hydrophobized m-FMSN conjugates with trimethylchlorosilane, $C_3H_9ClSi$, $^{29}$Si-nuclear magnetic resonance (NMR) spectrum shows M bands, which demonstrates the success of surface hydrophobization. Further, the conjugation of the modified molecule with smaller molecular weight after the hydrophobization can obtain M bands with the higher signals, and it is supposed that the initial hydrophobic molecule only modifies the outer surface of FMSN, but the volume and properties inside the pore are not affected.

Figure 5:
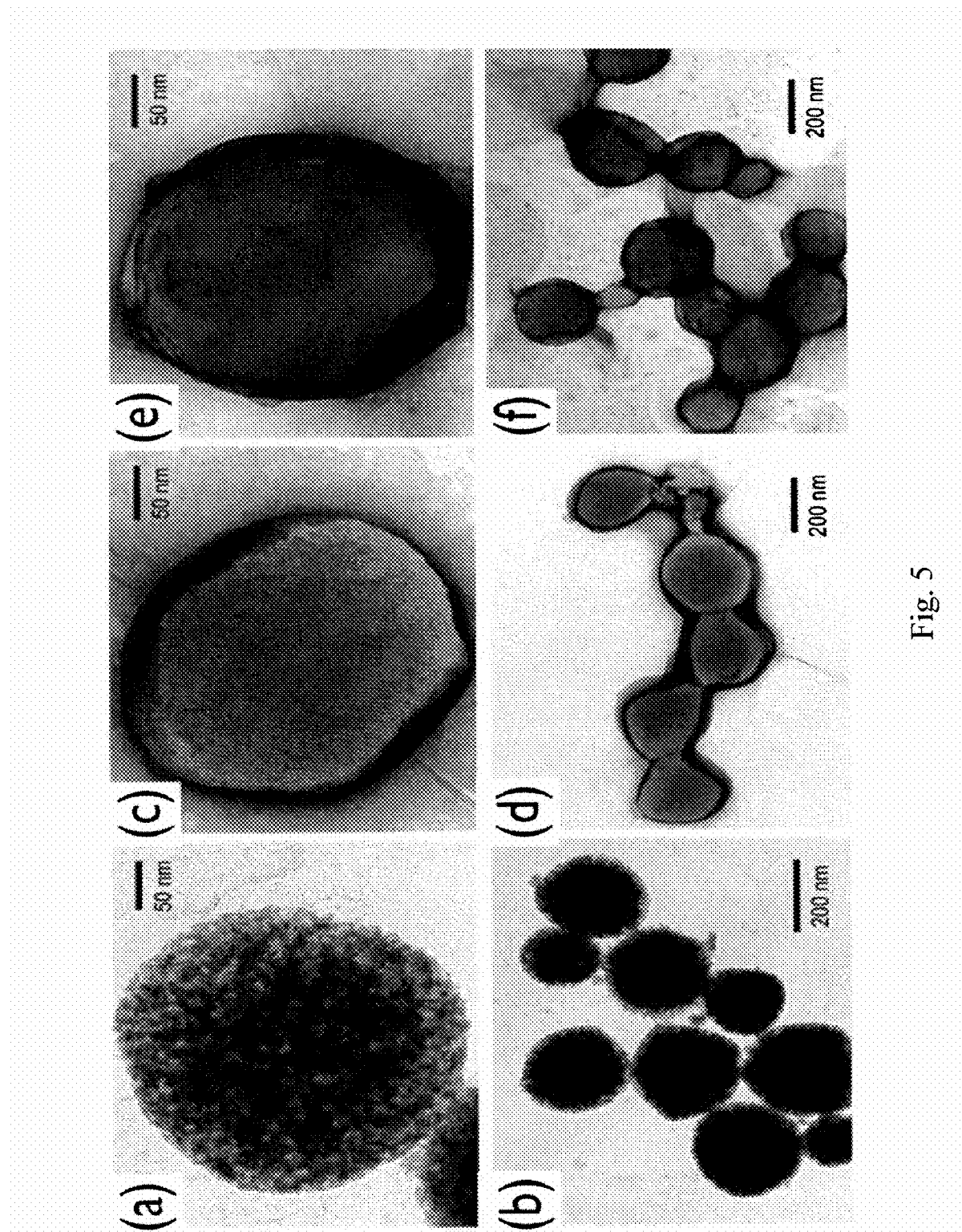
FIG. 5 illustrates the transmission electron microscopy of the FMSN before and after the phospholipid modification.

FIGS. 5a and 5b illustrate the transmission electron microscopy of FMSN with uranyl acetate staining. Stain is adsorbed into the pores of FMSN to result in the generation of the significant interpenetrating pattern in the FMSN due to electrostatic attraction. FIGS. 5c and 5d illustrate the transmission electron microscopy of m-FMSN. Because of the surface hydrophobicity, stain cannot enter the pores and can only accumulate in the periphery of the particles to form distinction, and porous structure can be observed in the top view of particles. FIGS. 5e and 5f illustrate the transmission electron microscopy of the phospholipid-coated MSN (LipoFMSN). Stain can be uniformly adsorbed in the periphery of particles due to the recovery of surface hydrophilicity, demonstrating that phospholipids actually encapsulate the surroundings of particle.

Figure 6A:
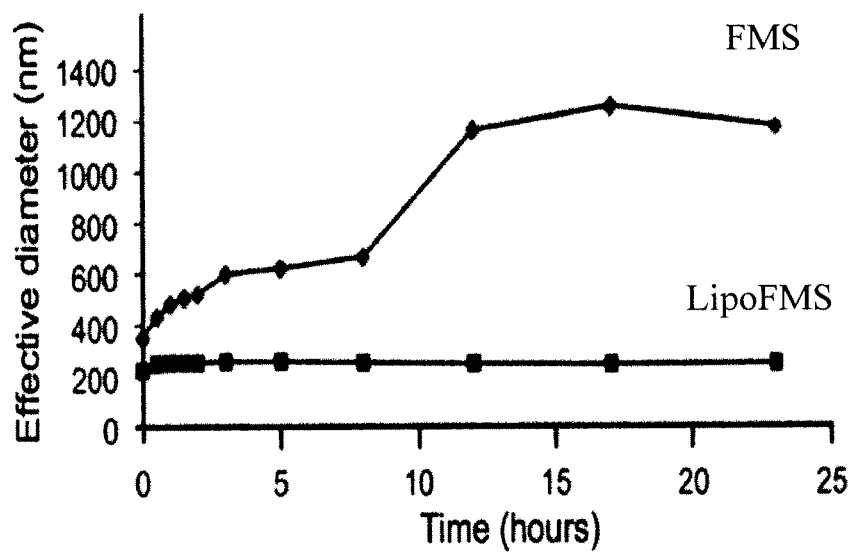
FIGS. 6a and 6b illustrate the comparison of aggregation between FMSN and LipoFMSN.
Figure 6B:
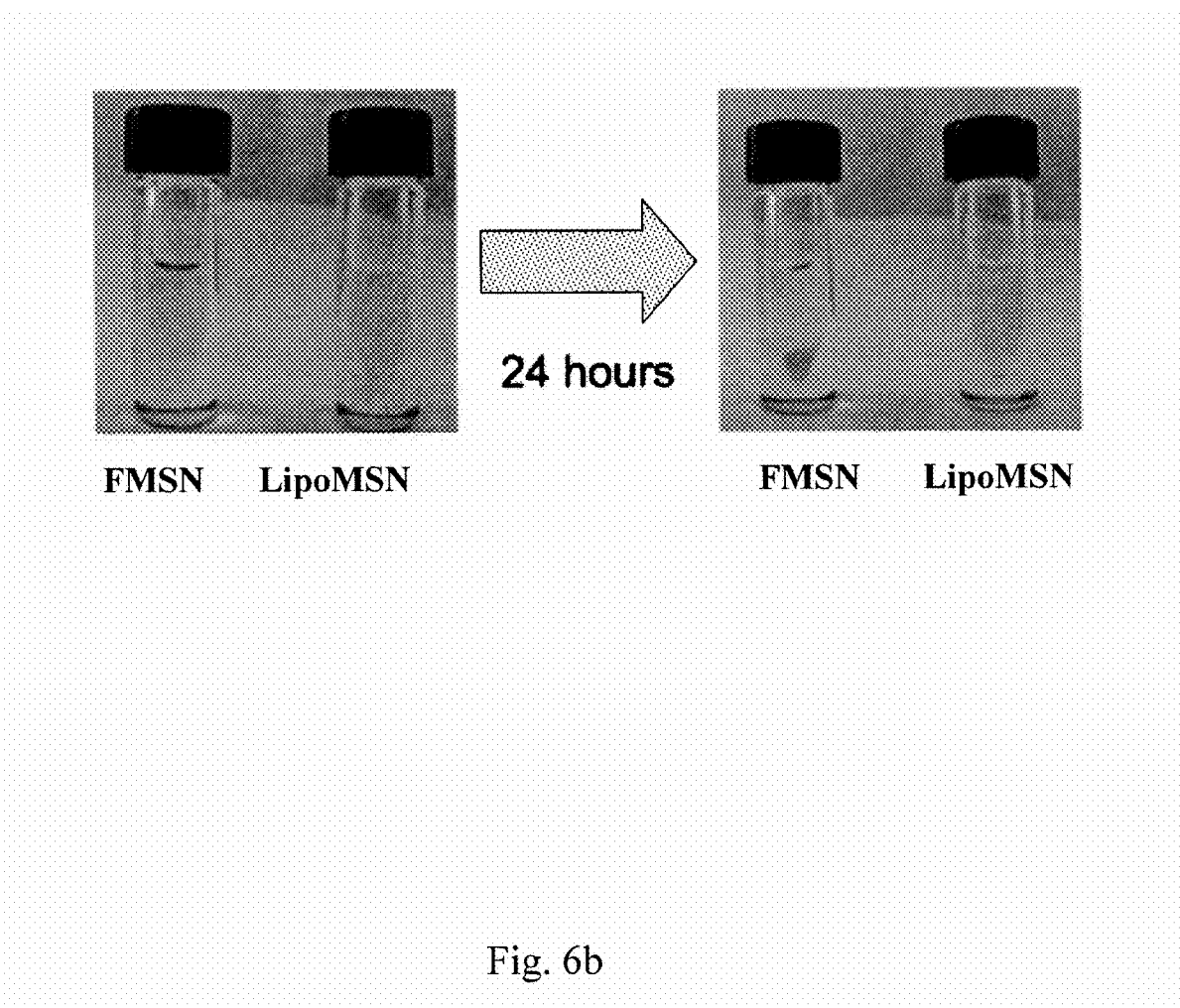

FIG. 6a illustrates particle size variance of FMSN in the phosphate buffer saline (PBS) with time before and after phospholipid encapsulation using dynamic light scattering particle size analyzer. It is found that LipoFMSN maintains its size in PBS, and no aggregation is generated over 24 hours. On the contrary, the regular FMSNs begin to aggregate in the PBS, and serious precipitation is happened after about 5 hours. The dispersion difference between LipoFMSN and FMSN in PBS after 24-hour deposition is significant.

Figure 7:
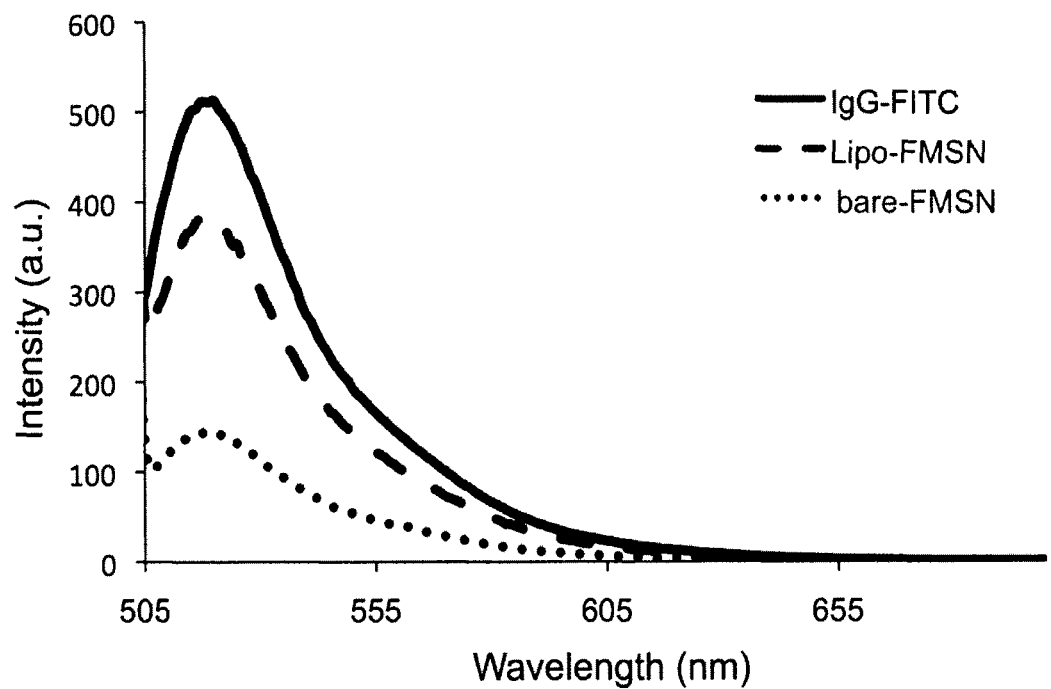
FIG. 7 illustrates the comparison of non-specific adsorption on protein between FMSN and LipoFMSN.

FIG. 7 illustrates the fluorescent intensity of IgG-FITC in the remaining solution determined after IgG-FITC mixs with MSN or LipoMSAN for 1 hour and then centrifugation. The highest fluorescence is the original fluorescence of IgG-FITC, and IgG-FITC fluorescence intensity in the MSN supplemented group decreases to 27.5% after centrifugation, indicating that 72.5% protein is non-specifically adsorbed on the MSN surface. However, if the IgG-FITC mixs with phospholipid-capped MSN, the remaining fluorescence is about 74%, indicating that non-specific adsorption of protein decreases to 26%.

Figure 8:
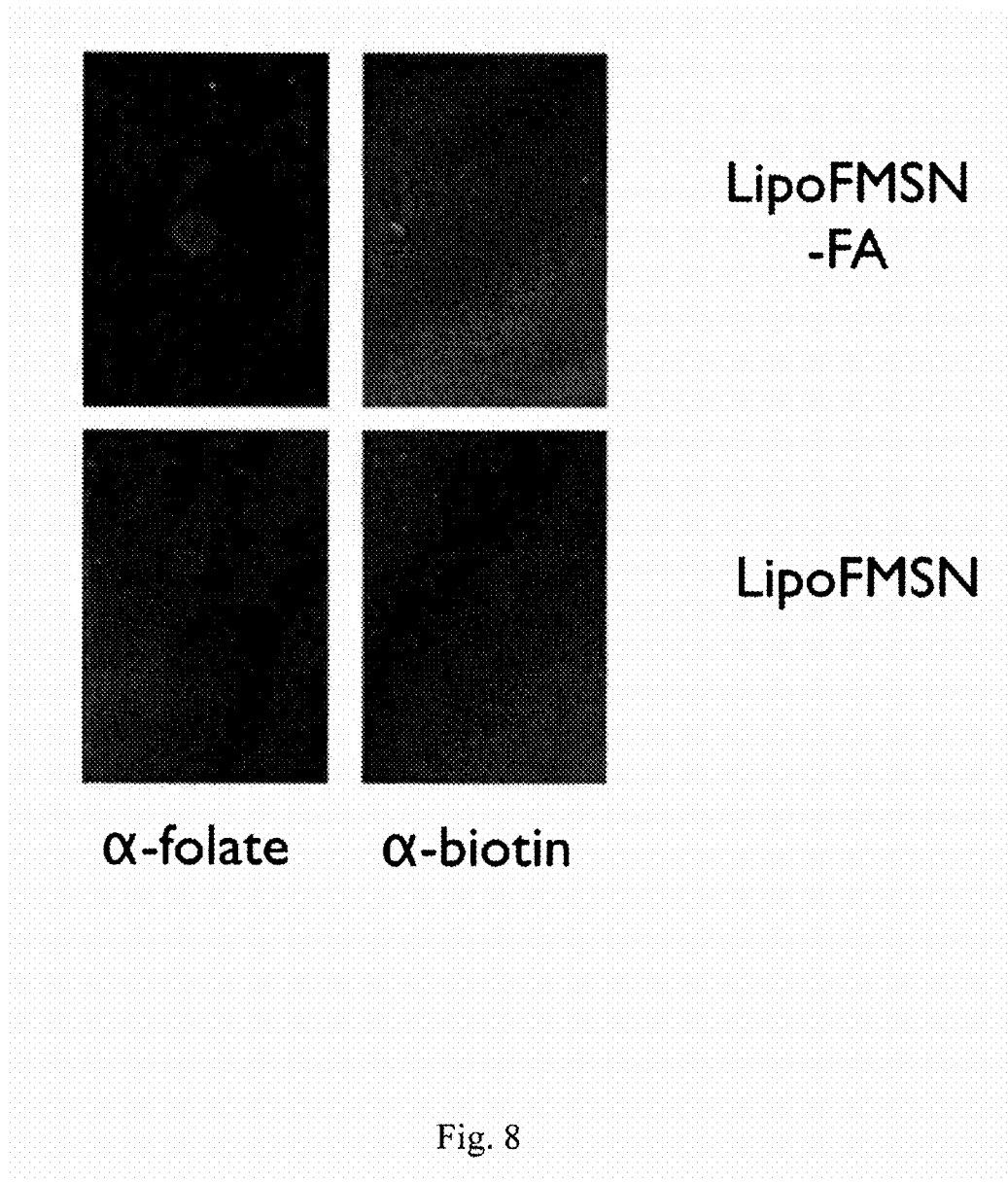
FIG. 8 illustrates the identification of folic acid-conjugated phospholipid-coated FMSN (LipoFMSN-FA) using immunoblotting method.

In order to achieve the function for targeting cancer cells, the folate-conjugated phospholipids (i.e. DSPE-PEG 2000-folate) is supplemented into the phospholipids-capped LipoFMSN in the present invention, and the identification is performed using immunoblotting assay. After anti-folic acid antibody and biotin antibody are dotted on the test paper, which then is incubated with LipoFMSN and LipoFMSN-FA, respectively, for 12 hours. As shown in FIG. 8, it is found that only LipoFMSN-FA conjugates anti-folic acid antibody after washing, so that the fluorescent signal is observed at the anti-folic acid antibody's dotted site. No non-specific binding is generated with respect to other antibody (biotin antibody), indicating the excellent specificity of LipoFMSN-FA.

Figure 9:
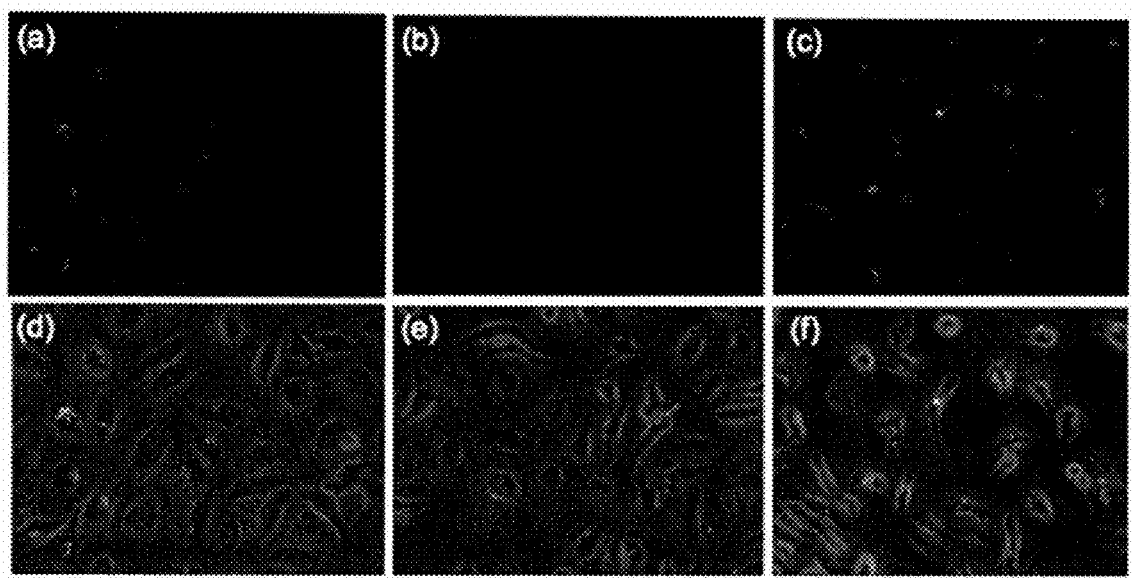
FIGS. 9a to 9i illustrates the comparison of cellular uptake after FSN, LipoFMSN and LipoFMSN-FA, respectively incubated with HeLa cells for 5 hours.
Figure 9G:
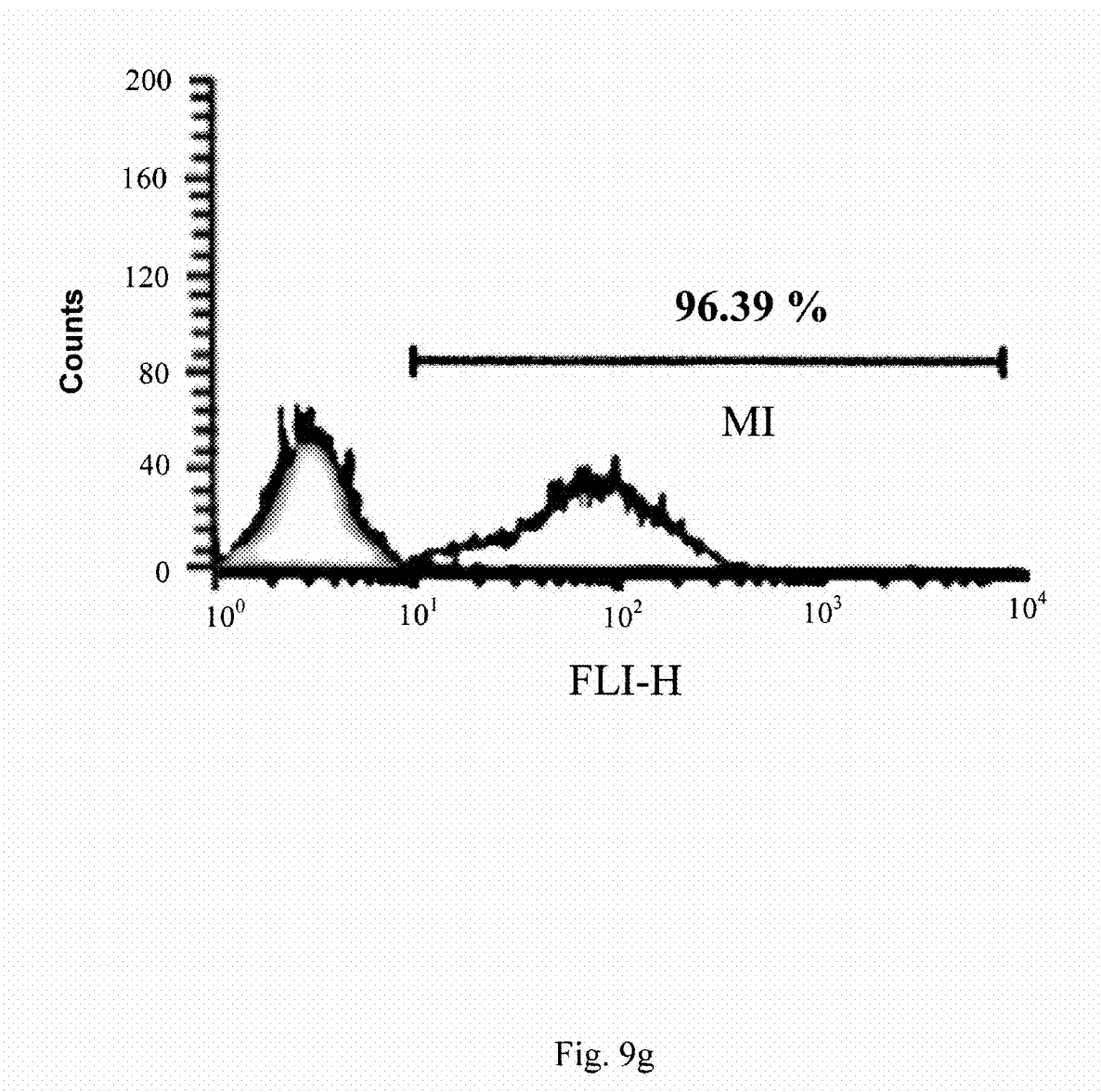
Figure 9H:
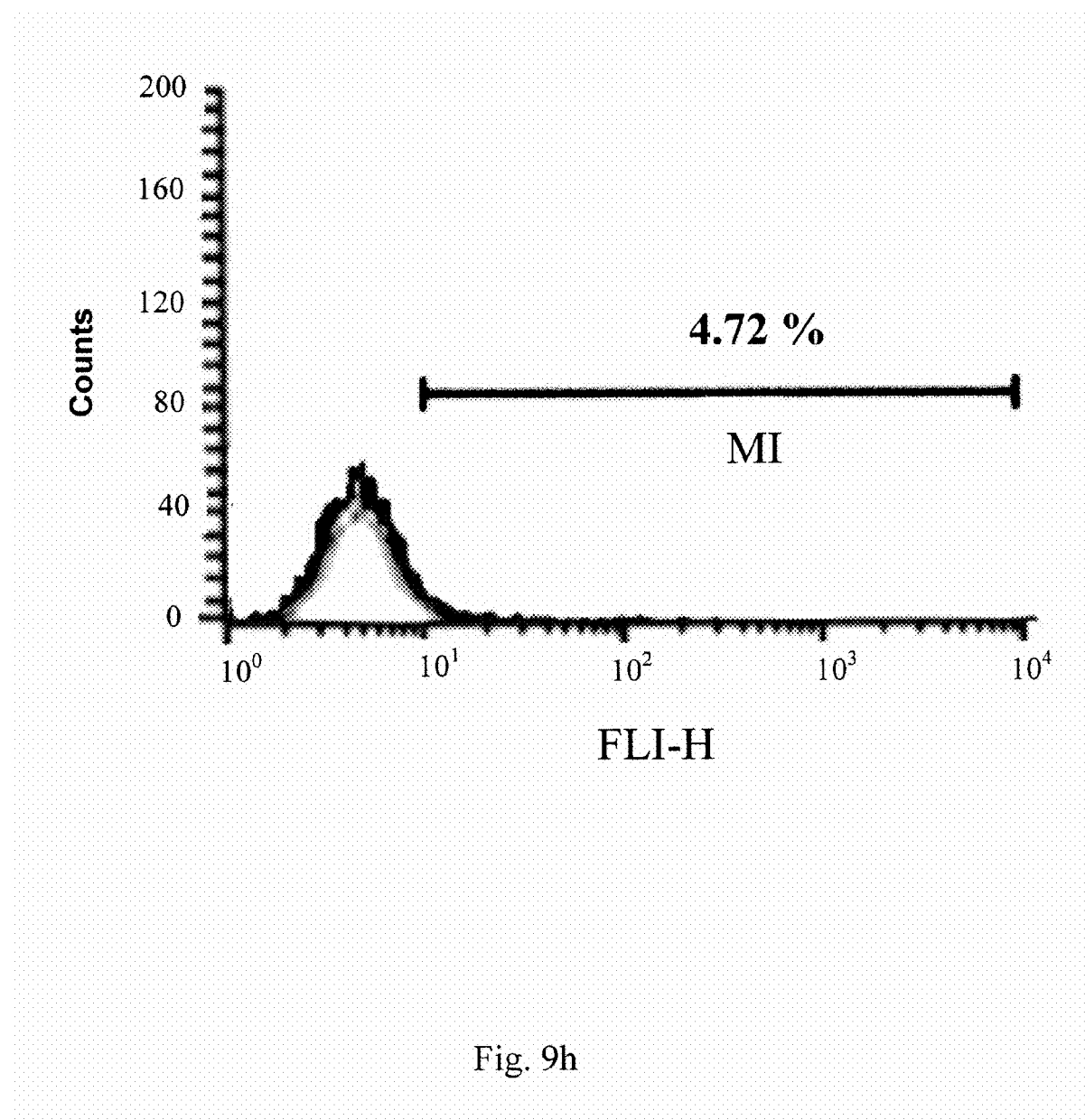
Figure 9I:
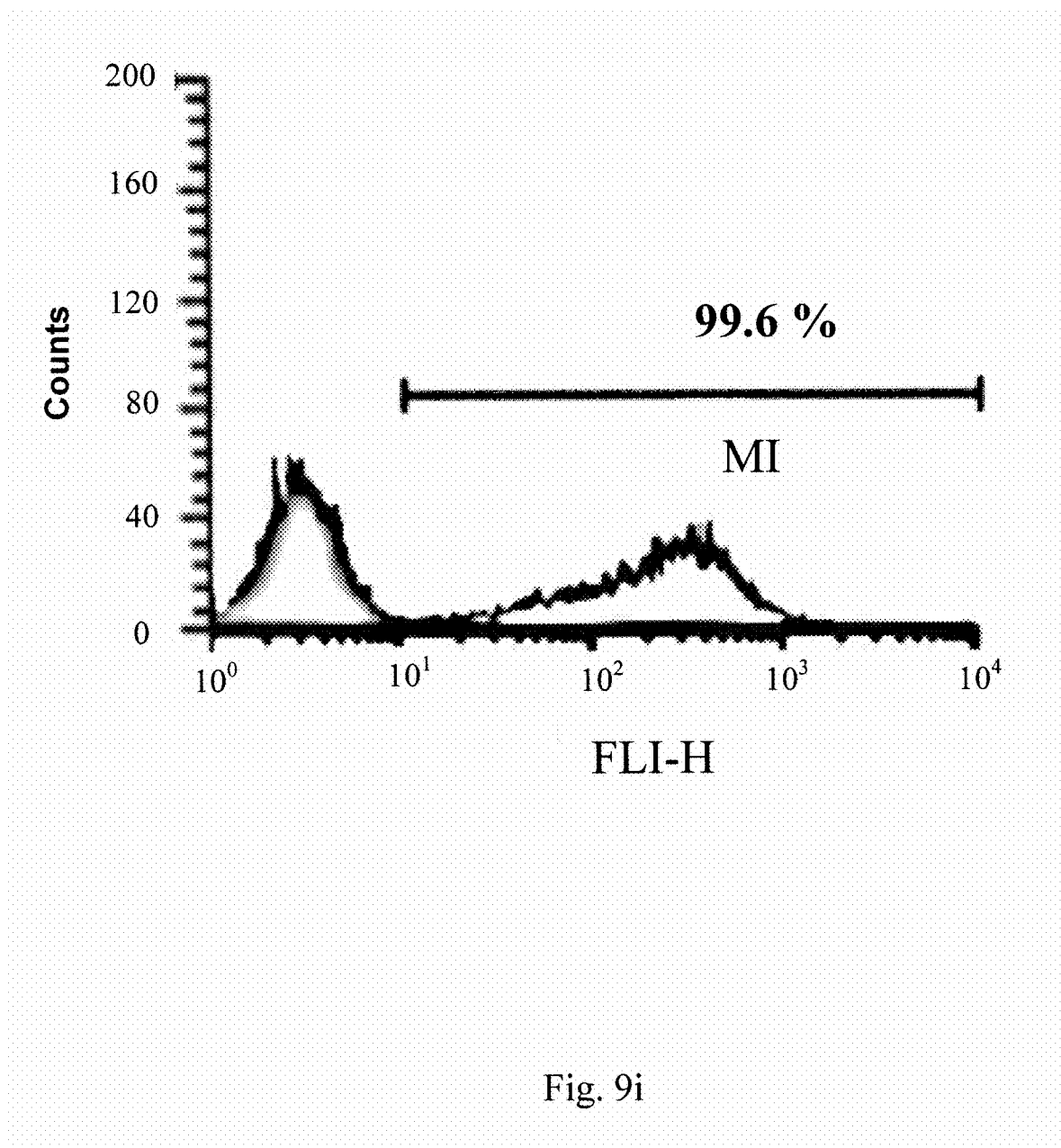

Cellular uptake of FMSN is observed in the fluorescent microscope after FMSN is incubated with HeLa cells for 5 hours. FIGS. 9a and 9b represents that the regular FMSN can be easily endocytosed due to the non-specific adsorption on cell membrane. The result analyzed from flow cytometry (FIG. 9g) represents 96.39% cells take up FMSN. FIGS. 9b and 9e are the results of HeLa cells incubated with LipoFMSN, showing cellular uptake of LipoFMSN is almost absent. FIG. 9h shows that only 4.72% cells take up LipoFMSN. Comparing with FMSN, the coating of phospholipids can effectively slow down the non-specific adsorption of FMSN on cell membrane and the non-specific uptake in cell. In LipoFMSN-FA group (FIGS. 9c and 9f), since folate receptor overexpresses on HeLa cell membrane, it recognizes and endocytoses LipoFMSN-FA, and thus 99.06% endocytosis is achieved.

Figure 10:
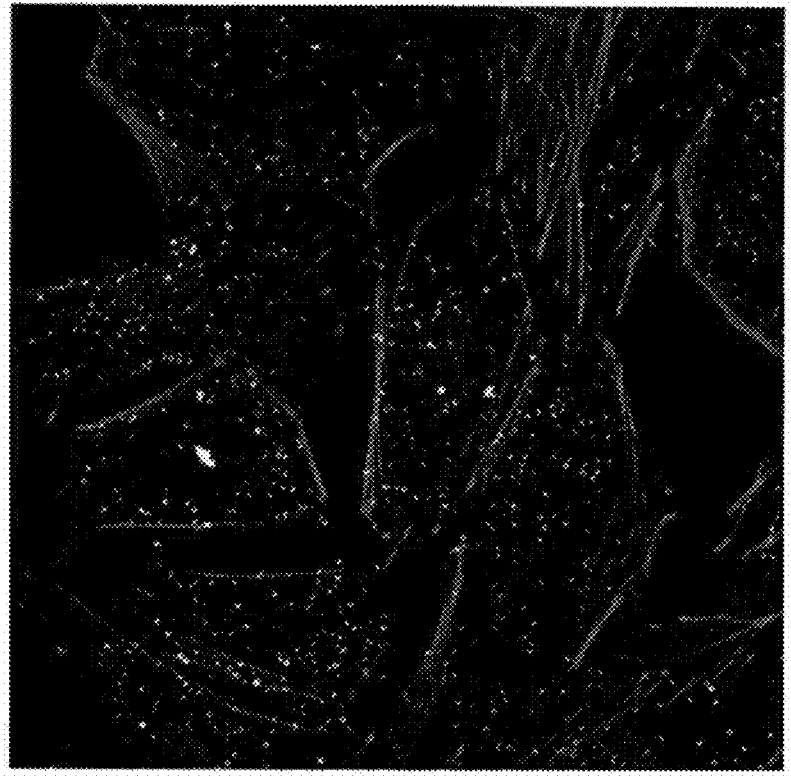
FIG. 10 illustrates the confocal microscopy of the cellular uptake of LipoFMSN-FA into HeLa cells.

After cells incubate with LipoFMSN-FA for 5 hours, cytoskeleton is stained with tetramethyl rhodamine isothiocyanate (TRITC)-phalloidin to show red fluorescence, and cell nucleus is stained with 4'-6-diamidino-2-phenylindole (DAPI) to show blue fluorescence. It is observed that LipoFMSN-FA actually enters into cells and uniformly disperse in the cytoplasm as chartreuse fluorescent dots by confocal microscopy (FIG. 10). Furthermore, after LipoFMSN-FA enters into HeLa cells and incubates for 24 hours, it is found that this material does not have significant cytotoxicity.

While the invention has been described in terms of what is presently considered to be the most practical and preferred Embodiments, it is to be understood that the invention needs not be limited to the disclosed Embodiments. On the contrary, it is intended to cover various modifications and similar arrangements included within the spirit and scope of the appended claims, which are to be accorded with the broadest interpretation so as to encompass all such modifications and similar structures.

What is claimed is:

1. A multilayer vehicle, comprising:
   a mesoporous silica core;
   a 13-(chlorodimethylsilylmethyl)-heptacosane layer having a first terminal conjugated to a surface of the silica nanoparticle; and
   a lipid monolayer modified on a second terminal of the hydrophobic molecule.

2. The multilayer vehicle according to claim 1, wherein the silica nanoparticle has a pore ranged between 2 nm and 50 nm.

3. The multilayer vehicle according to claim 1, wherein the lipid layer has a surface comprising a functional molecule.

4. The multilayer vehicle according to claim 3, wherein the functional molecule comprises a target molecule, a genomic material, an aptamer, a protein, an antibody, a contrast agent and a folic acid.

5. The multilayer vehicle according to claim 2 further comprising an active material encapsulated in the pore of the silica nanoparticle.

6. The multilayer vehicle according to claim 5, wherein the active material is one selected from a group consisting of a drug, a fluorescent agent, a protein, a polypeptide, an antibody, a radioactive material, a growth factor, an aptamer, and a genomic material.

7. The multilayer vehicle according to claim 5, wherein the multilayer vehicle is a nanoshuttle.

8. The multilayer vehicle according to claim 7, wherein the nanoshuttle is delivered by one selected from a group consisting of an oral administration, a transdermal, an injection and an inhalation.

* * * * *